United States Patent [19]
Balzer et al.

[11] Patent Number: 5,645,610
[45] Date of Patent: Jul. 8, 1997

[54] SUBSTITUTED 2-ALKYLAMINO-4-AMINO-1-ALKYLBENZENE COMPOUNDS AND OXIDATION HAIR DYE COMPOSITIONS BASED ON SAID COMPOUNDS

[76] Inventors: Wolfgang R. Balzer, Schlesier Strasse 9a, 64665 Alsbach; Anke Frank, Alte Falterstrasse 29, 65933 Frankfurt; Alexa Weinges, Langgewann 9, 69121 Heidelberg, all of Germany

[21] Appl. No.: 450,476

[22] Filed: May 26, 1995

[30] Foreign Application Priority Data

Jun. 18, 1994 [DE] Germany ............... 44 21 397.2

[51] Int. Cl.$^6$ .............. A61K 7/13; C07C 209/00
[52] U.S. Cl. ................. 8/411; 8/406; 8/407; 8/408; 8/409; 8/416; 564/305; 564/442; 564/443
[58] Field of Search ............... 8/406, 407, 408, 8/409, 411, 412, 416; 564/305, 306, 442, 443

[56] References Cited

U.S. PATENT DOCUMENTS

| | | | |
|---|---|---|---|
| 4,566,875 | 1/1986 | Grollier et al. | 8/411 |
| 4,854,935 | 8/1989 | Clausen et al. | 8/416 |
| 4,997,451 | 3/1991 | Clausen et al. | 8/408 |
| 5,061,289 | 10/1991 | Clausen et al. | 8/416 |
| 5,143,518 | 9/1992 | Madrange et al. | 8/416 |
| 5,224,965 | 7/1993 | Clausen et al. | 8/408 |

FOREIGN PATENT DOCUMENTS

| | | |
|---|---|---|
| 3622784 | 1/1988 | Germany . |
| 4028661 | 3/1992 | Germany . |
| 4206416 | 9/1993 | Germany . |
| 60-193950 | 10/1985 | Japan . |
| 2216124 | 10/1989 | United Kingdom . |

*Primary Examiner*—Paul Lieberman
*Assistant Examiner*—Caroline L. Dusheck
*Attorney, Agent, or Firm*—Michael J. Striker

[57] ABSTRACT

The new coupler compounds of the invention are 4-amino-2-(2'-hydroxyethyl)-amino-5-methoxytoluene and/or 4-amino-2-(2'-hydroxyethyl)amino-5-chlorotoluene. The invention also includes an oxidation hair dye composition including an effective amount, advantageously from 0.01 to 5 percent by weight, of the above-mentioned new coupler compounds together with one or more known developer compounds and optionally certain direct dyes.

7 Claims, No Drawings

SUBSTITUTED 2-ALKYLAMINO-4-AMINO-1-ALKYLBENZENE COMPOUNDS AND OXIDATION HAIR DYE COMPOSITIONS BASED ON SAID COMPOUNDS

BACKGROUND OF THE INVENTION

The present invention relates to new 5-position-substituted 2-alkylamino-4-amino-1-alkylbenzene compounds and oxidation hair dye compositions or agents for dyeing hair based on the use of the new 5-position-substituted 2-alkylamino-4-amino-1-alkylbenzene compounds as coupler substances.

Oxidation hair dyes have attained substantial importance in hair dye practice. A hair dyeing mixture is produced by oxidative coupling of developer substance and coupler substance on the hair shaft. This leads to a very intensive hair dyeing with very good color fastness. Furthermore different color shades can be produced by combination of appropriate developer and coupler substances.

Advantageously 2,5-diaminotoluene, 1,4-diaminobenzene, 2-(2'-hydroxyethyl)-1,4-diaminobenzene, 4-aminophenol, 4-amino-2-aminomethylphenol and 4-amino-3-methylphenol and substituted 4,5-diaminopyrazoles can be used as developer substances.

m-phenylenediamine and its derivatives such as 2,4-diaminophenoxyethanol, 2-amino-4-(2'-hydroxyethyl) aminoanisole or pyridine derivatives such as 3,5-diamino-2,6-dimethoxypyridine as a blue coupler, 1-naphthol, m-aminophenol and its derivatives such as 2-amino-4-chloro-6-methylphenol, 5-amino-2-methylphenol, 4-amino-2-hydroxyphenoxyethanol, 4-amino-5-fluoro-2-hydroxytoluene and 4-amino-5-ethoxy-2-hydroxytoluene as red couplers and resorcin, 4-chlororesorcin, 4,6-dichlororesorcin, 2-methylresorcin, 4-hydroxy-1,2-methylenedioxybenzene, 4-(2'hydroxyethyl)amino-1,2-methylenedioxybenzene and 4-hydroxyindole as couplers for brown-blond shades are all advantageously useful as coupler substances.

Oxidation hair dyes which are used to dye human hair must meet numerous special requirements. They must be unobjectional in regard to their toxicological and dermatological properties and they must dye with the desired color intensity. Furthermore a satisfactory light fastness, permanent wave fastness, acid fastness and friction fastness is required for the desired hair dye compounds. In each case the hair dye compounds must be stable to light, friction and chemical agents over a period of at least 4 to 6 weeks. Also it is necessary that a broad palette of various color shades can be obtained by combination of appropriate coupler and developer substances.

The coupler substances currently used, particularly for providing red and blue color shades, however do not meet these requirements in a completely satisfactory manner. Similarly these substances do not have the best dermatological properties for many applications. It has thus been necessary to find additional coupler substances with improved dermatological and toxicological properties. Furthermore these compounds have disadvantageous stability problems, particularly a premature bleaching under the influence of light.

The 5-halogen-2,4-bis-(alkylamino)-1-alkylbenzene disclosed in German Laid-Open Patent Application DE-OS 42 06 416 shows no mutagenic effect in an Ames test, however the color intensity of the dyed hair obtained with this coupler substance is not always satisfactory because of its solubility.

The coupler substances 2,4-diamino-5-ethoxytoluene and 2,4-diamino-5-(2'-hydroxyethyl)oxytoluene described in German Laid-Open Patent Application DE-OS 36 22 784 have of course good toxicological properties, however they produce only weak dyed colors when used with developers such a p-aminophenol or its derivatives.

5-fluoro-2,4-diaminotoluene described in German Laid-Open Patent Application DE-OS 40 28 661 shows no mutagenic effect, however the stability of the hair colors produced with this coupler substance to light is not satisfactory.

SUMMARY OF THE INVENTION

It is an object of the present invention to provide an oxidation hair dye composition for dyeing of hair based on a content of a standard known developer substance and a new coupler substance in which the above-described requirements of the significant properties of the new coupler substances are fulfilled.

It has now been found that an oxidation hair dye composition based on a developer-coupler combination and, if necessary, other dye compounds and conventional cosmetic additives, which contains at least one coupler substance of the formula (I):

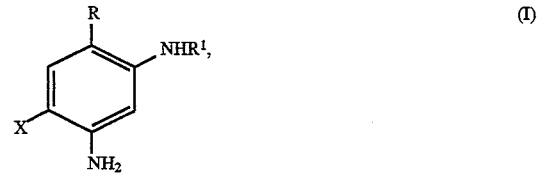

in which R represents a straight chain or branched $C_1$- to $C_4$-alkyl group, X represents chlorine or a straight chain or branched $C_1$- to $C_4$-alkoxy group and $R^1$ represents a straight chain or branched $C_1$- to $C_4$-alkyl group or a straight chain or branched $C_2$- to $C_4$-hydroxyalkyl group; or a physiologically compatible water soluble salt thereof; satisfies the above-described object of the invention in an outstanding manner.

In contrast it has also been found that the compounds of formula (II) hereinbelow

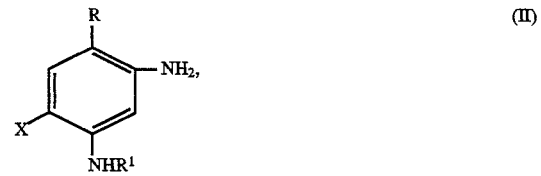

which are isomeric to the compounds of formula (I) and in which R, X and $R^1$ have the above-described significance and similar compounds which are not substituted in the 5-position do not provide dyed hair colors of sufficient fastness.

The coupler substances of the formula (I) are obtained by simple chemical reactions from commercially available starting materials and produce with developer substances such as p-phenylenediamine clear blue shades without reddish tones. With developers of the p-aminophenol type deep red shades can be obtained, whose color intensity is even greater than the dyed colors obtained with the unsubstituted 2-alkylamino-4-amino-1-alkylbenzene.

The coupler substances of the formula (I) are water soluble and have an outstanding shelf or storage stability, especially as components of the hair dye compositions described here.

The hair dye compositions described here should contain the coupler substance according to the invention of formula (I) in an effective amount sufficient to dye hair, advantageously in an amount of from 0.01 to 5 percent by weight, particularly advantageously from 0.1 to 3 percent by weight.

4-amino-2-(2'-hydroxyethyl)amino-5-ethoxytoluene, 4-amino-2-(2'-hydroxyethyl)amino-5-methoxytoluene and 4-amino-2-(2'-hydroxyethyl)amino-5-chlorotoluene, are particularly preferred as coupler substances of the formula (I) in the oxidation hair dye composition.

At least one additional coupler substance can be contained in the oxidation hair dye composition according to the invention in an amount from 0.01 to 5 percent by weight, advantageously 0.1 to 3 percent by weight. These additional coupler substances can be for example resorcin, 4-chlororesorcin, 4,6-dichlororesorcin, 2-methylresorcin, 2-amino-4-(2'-hydroxyethylamino)anisole, 4-amino-5-fluoro-2-hydroxytoluene, 4-amino-5-ethoxy-2-hydroxytoluene, m-phenylenediamine, 5-amino-2-methylphenol, 2,4-diaminophenoxyethanol, 1-naphthol, m-aminophenol, 3-amino-4-chloro-6-methylphenol, 3-amino-2-methylphenol, 4-amino-2-hydroxyphenoxyethanol, 4-hydroxy-1,2-methylenedioxybenzene, 4-(2'-hydroxyethylamino)-1,2-methylenedioxybenzene, 2,4-diamino-5-ethoxytoluene, 4-hydroxyindole and 3,5-diamino-2,6-dimethoxy pyridine.

The developer substances for the hair dye composition according to the invention can include 1,4-diaminobenzene, 2,5-diaminotoluene, 2-(2'-hydroxyethyl)-1,4-diaminobenzene, 4-aminophenol, 4-amino-2-aminomethylphenol, 4-amino-3-methylphenol, 4-amino-2-methoxymethylphenol, 4-amino-2-ethoxymethylphenol, 4,5-diamino-1-methylpyrazole, 4,5-diamino-1-isopropyl pyrazole, 1-benzyl-4,5-diamino pyrazole, 4,5-diamino-1-methylbenzyl pyrazole and tetraaminopyrimidine or their physiologically compatible salts. These developer substances are contained in the hair dye composition according to the invention advantageously in an amount of from 0.01 to 5 percent by weight, particularly advantageously however from 0.1 to 3.0 percent by weight.

The conventional coupler and developer substances can be contained in the hair dye composition according to the invention individually, or in a mixture with others. The total amount of the developer-coupler combination contained in the hair dye composition described here should amount to about 0.1 to 5.0 percent by weight, advantageously 0.5 to 4.0 percent by weight.

The developer substances are used generally in about equimolar quantities, relative to the coupler substances. It is however not disadvantageous when the developer substances are present in a certain excess relative to the coupler substances present or when the coupler substance is present in excess relative to the developer substances.

Furthermore self-coupling dyes or direct dyes can also be included in the hair dye compositions according to the invention. These self-coupling dyes or direct dyes can include, for example, 6-amino-2-methylphenol and 2-amino-5-methylphenol as well as additional conventional direct dyes, for example triphenylmethane dye compounds such as 4-[(4'-aminophenyl)-(4"-imino-2",5"-cyclohexadien-1"-yliden)methyl]-2-methylaminobenzene monohydrochloride (C.I. 42 510), 4-[(4'-amino-3'-methylphenyl) -(4"-imino-3"-methyl-2",5"-cyclohexadien-1"-yliden)methyl]-2-methylaminobenzene monohydrochloride (C.I. 42 520), aromatic nitro dye compounds such as 2-amino-4,6-dinitrophenol, 2-amino-5-(2'-hydroxyethylamino)-nitrobenzene and 4-(2'-hydroxyethylamino)-3-nitrotoluene, 1-(2'-ureidoethyl) amino-4-nitrobenzene and azo dye compounds such as 7-[(4'-aminophenyl)azo]-8-hydroxynaphthalen-4-sulfonic acid sodium salt (C.I. 14 805) and disperse dye compounds such as 1,4-diaminoanthraquinone and 1,4,5,8-tetraaminoanthraquinone. These self-coupling dyes or direct dye compounds can be included in the hair dye composition according to the invention in amounts of from 0.1 to 4 percent by weight.

Additional suitable hair dye compounds are described for example in the book by J. C. Johnson, "Hair Dyes", Noyes Data Corp., Park Ridge, USA (1973), pp 3 to 91 and 113 to 129 (ISBN: 0-8155-0477-2).

The coupler and developer substances and the other dye components, in so far as they are bases, can be used understandably also in the form of physiologically acceptable or compatible acid addition salts, for example as their hydrochlorides or sulfates, or—in so far as they have OH groups—in the form of salts with bases, for example as an alkali metal phenolate.

Furthermore conventional cosmetic additives can be present in the hair dye compositions according to the invention. These conventional cosmetic additives can include antioxidants such as ascorbic acid, thioglycolic acid or sodium sulfite, perfume oils, complex formers, wetting agents, emulsifiers, thickeners, hair care components and other additives.

The preparation used can be for example in the form of a solution, especially an aqueous-alcoholic solution. The particularly preferred forms of the preparation are however a cream, a gel or an emulsion. The composition of the preparation comprises a mixture of the above-described dye components with the conventional additives used in the preparation.

Additional additives for hair dye compositions according to the invention in the form of solutions, creams, emulsions or gels include, for example, solvents such as water, lower aliphatic alcohols such as ethanol, propanol and isopropanol or glycols such as glycerin and 1,2-propylene glycol, wetting agents or emulsifiers chosen from the categories of anionic, cationic, amphoteric or nonionic surface active substances such as fatty alcohol sulfates, ethoxylated fatty alcohol sulfates, alkylsulfonates, alkylbenzene sulfonates, alkyltrimethylammonium salts, alkylbetains, ethoxylated fatty alcohols, ethoxylated nonylphenol, fatty acid alkanol amides, ethoxylated fatty acid esters, thickeners such as higher fatty alcohols, starches or cellulose derivatives, petrolatum, paraffin oil and fatty acids as well as hair care materials such as cationic resins, lanolin derivatives, cholesterin, pantothenic acids and betaine. The above-mentioned conventional components are used in amounts which are standard for their particular purpose, e.g. the wetting agents and emulsifiers in concentrations of about 0.5 to 30 percent by weight, the thickeners in amounts of from about 0.1 to 25 percent by weight and the hair care materials in a concentration of about 0.1 to 5.0 percent by weight.

The hair dye composition according to the invention can be weakly acidic, neutral or alkaline according to its composition. The pH of the hair dye composition particularly can be from 6.0 to 11.5. The pH of the composition can be adjusted successfully with ammonia, but it can also be adjusted with an organic amine, for example monoethanolamine and triethanolamine, or also an inorganic base such as sodium hydroxide and potassium hydroxide.

The method of using the oxidation hair dye composition according to the invention includes mixing the above-described hair dye composition directly prior to use with an oxidizing agent and applying the mixture to the hair in a sufficient amount to dye the hair, according to the amount of hair present, generally in an amount of from 60 to 200 g.

The oxidizing agent or composition for developing the hair dye includes principally hydrogen peroxide or its addition compounds to urea, melamine or sodium borate in the form of a 3 to 12 percent, advantageously 6 percent, aqueous solution. Similarly it is possible to develop the color by action of atmospheric oxygen, which means without addition of an oxidizing agent. If a 6-percent hydrogen peroxide solution is used, the weight ratio of hair dye composition according to the invention and oxidizing agent amounts to 5:1 to 1:2, advantageously however 1:1. Larger amounts of oxidizing agent are used particularly when there is a high dye compound concentration in the oxidation hair dye composition or when at the same time a comparatively stronger bleaching of the hair is intended.

In the method of using the hair dye composition according to the invention the mixture of the oxidizing agent and the hair dye composition is allowed to act on the hair at 15° to 50° C. for from 10 to 45 minutes, advantageously 30 minutes, the hair is rinsed with water and dried. If necessary in connection with the rinsing a shampoo is used to wash the hair and eventually an after-rinse is performed with a weak organic acid, such as citric acid or tartaric acid. Subsequently the hair is dried.

The hair dye composition according to the invention provide a hair dyeing with outstanding fastness properties, particular an outstanding light fastness, washing fastness and friction fastness and may be stripped with reducing agents. It also provides a broad palette of different hair color shades and nuances according to its type and composition. The color intensity of the red colors and color purity of blue colors obtained with the hair dyeing composition according to the invention are particularly noteworthy. Finally a coloring or dyeing of gray and chemically undamaged hair is problem-free when the hair dye composition according to the invention is used and a very good color coverage is obtained. The colors produced using the hair dye composition according to the invention are both uniform and very satisfactorily reproducible independently of the differing hair structures to which it is applied.

The new 5-position-substituted 2-alkylamino-4-amino-1-alkylbenzene compounds of the formula (I) can be easily made from the commercially available 2-amino-1-alkyl benzenes of formula (III). The 2-amino-1-alkyl benzenes of formula (III) are nitrated at the 4-position to obtain the corresponding 2-amino-5-halogen-4-nitro-1-alkylbenzene of formula (IV):

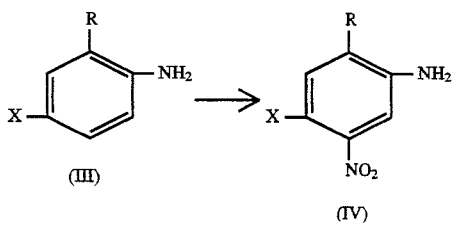

The standard nitrating reagents used in organic synthesis can be used to perform the above nitration including advantageously a mixture of sulfuric acid and nitric acid.

The new coupler substances of formula (I) can be made in two ways from the 2-amino-5-halogen-4-nitro-1-alkylbenzene (IV):

1. The 2-amino-5-halogen-4-nitro-1-alkylbenzene is reacted with the corresponding $C_2$- to $C_4$-chloroformic acid-chloroalkylester to from the hydroxyalkylated compound of formula (V) shown below, in which $R^2$ is a straight chain or branched $C_2$- to $C_4$-hydroxyalkyl residue and R and X have the same meaning as described hereinabove. The reduction of the nitro group is performed with reagents suitable for this step, for example hydrogen in the presence of a suitable catalyst, especially palladium/activated charcoal, and the product is the hydroxyalkylated compound according to the invention of formula (Ia):

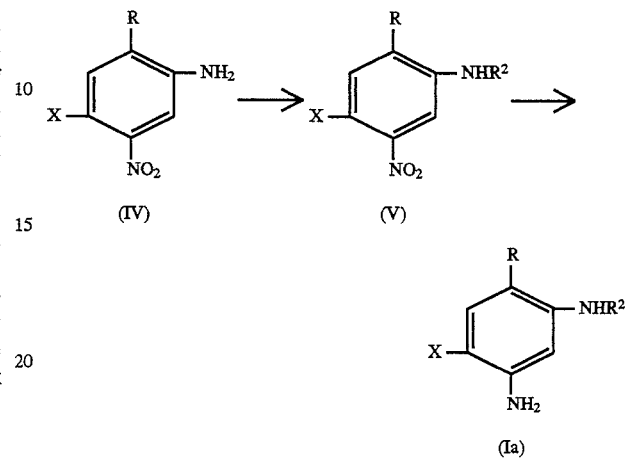

2. The compounds of formula (Ib), in which the amino groups are substituted with a straight or branched $C_1$- to $C_4$-alkyl group may be made from the corresponding 2-amino-5-halo-4-nitro-1-alkylbenzene (IV) in four synthesis steps according to the following reaction scheme by reaction with a standard protective group reagent for the amino group, for example benzene sulfonyl chloride, alkylation with a standard alkylating agent, for example a $C_1$- to $C_4$-alkyl iodide and subsequent removal of the protective group followed by reduction of the nitro group, wherein $R^3$ represents a straight chain or branched $C_1$- to $C_4$-alkyl group and Y represents a standard protective group for the amino group and R and X have the same significance as above.

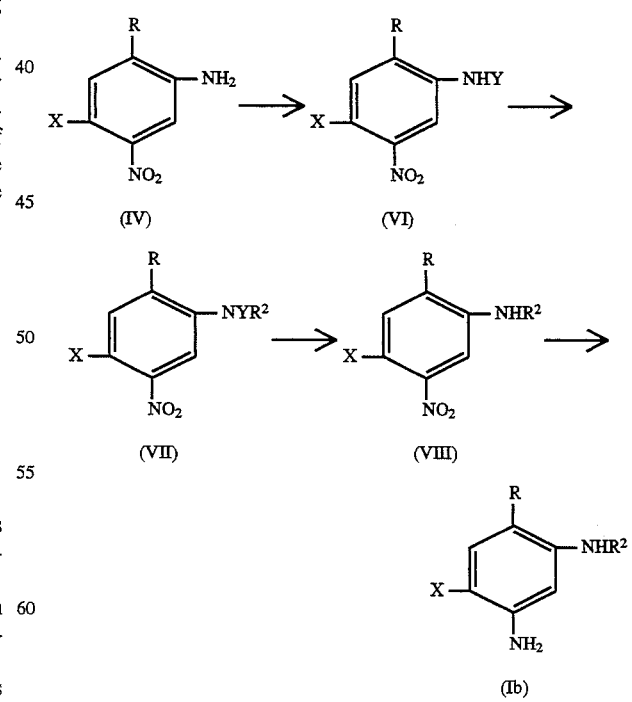

The following examples should illustrate the preferred embodiments without limiting the claims appended hereinbelow.

EXAMPLES

Examples of Hair Dye Compositions

| Example 1 | Hair Dye Composition in the form of a Gel |
|---|---|
| 0.08g | 4-amino-2-(2'-hydroxyethyl)amino-5-methoxytoluene |
| 1.00g | 2-(2'hydroxyethyl)-1,4-diaminobenzene sulfonate |
| 0.35g | resorcin |
| 0.05g | m-aminophenol |
| 0.40g | sodium sulfite, water free |
| 15.00g | oleic acid |
| 7.00g | isopropanol |
| 10.00g | ammonia (22 percent by weight aqueous solution) |
| 66.12g | water |
| 100.0 | |

50 g of the above hair dye composition in gel form are mixed with 50 ml of a 6% by weight hydrogen peroxide solution shortly before the mixture is to be used to dye hair. The mixture is then applied to blond human hair. After a acting time of thirty minutes at 40° C. the hair is rinsed with water and then dried. The hair after it is dyed with the mixture has a natural brown color.

| Example 2 | Hair Dye Solution |
|---|---|
| 0.22g | 4-amino-2-(2'-hydroxyethyl)amino-5-methoxytoluene |
| 1.26g | p-aminophenol |
| 0.12g | resorcin |
| 0.10g | m-aminophenol |
| 1.05g | 5-amino-2-methylphenol |
| 0.40g | sodium sulfite, water free |
| 10.00g | lauryl alcohol-diglycolethersulfate (28% aqueous solution) |
| 10.00g | isopropanol |
| 20.00g | ammonia (22 percent aqueous solution) |
| 56.85g | water, completely free of salt |
| 100.0 | |

50 g of the above-described hair dye solution are mixed with 50 ml of a 6 percent hydrogen peroxide solution shortly prior to application on the hair. The mixture is then applied to blond human hair. After an acting time of thirty minutes at forty degrees Celsius the hair is rinsed with water and dried. The hair is dyed a fashionable Bordeaux red.

Comparative Example

For comparison of the color of hair dyed with the hair dye compounds of formula (I) and those of the prior art a hair dye solution is prepared with an equimolar quantity of a known developer substance which is either 1,4-diaminobenzene (Examples I, IV, VII and X)

2,5-diaminotoluene (Examples II, V, VIII and XI) or 2-(2'-hydroxyethyl)-1,4-diaminobenzene (Examples III, VI, IX and XII) in combination with one of the coupler substances of formula (I), 4-amino-2-(2'-hydroxyethyl)amino-5-methoxytoluene or 4-amino-2-(2'-hydroxyethyl)amino-5-chlorotoluene or a known coupler substance, 2,4-diamino-5-ethoxytoluene or 2,4-diamino-5-fluorotoluene.

| Comparison Example I | Hair Dye Solution |
|---|---|
| 10.0000g | of a mixture of the potassium salt of coconut oil fatty acid and oleic acid |
| 10.0000g | isopropanol |
| 2.4531g | 4-amino-2-(2'-hydroxyethyl)amino-5-methoxytoluene |
| 1.3518g | 1,4-diaminobenzene |
| 10.0000g | ammonia (25 percent aqueous solution) |
| 66.1951g | water |
| 100.0 | |

| Comparison Example II | Hair Dye Solution |
|---|---|
| 10.0000g | of a mixture of the potassium salt of coconut oil fatty acid and oleic acid |
| 10.0000g | isopropanol |
| 2.4531g | 4-amino-2-(2'-hydroxyethyl)amino-5-methoxytoluene |
| 1.5271g | 2,5-diaminotoluene |
| 10.0000g | ammonia (25 percent aqueous solution) |
| 66.0198g | water |
| 100.0 | |

| Comparison Example III | Hair Dye Solution |
|---|---|
| 10.0000g | of a mixture of the potassium salt of coconut oil fatty acid and oleic acid |
| 10.0000g | isopropanol |
| 2.4531g | 4-amino-2-(2'-hydroxyethyl)amino-5-methoxytoluene |
| 1.9025g | 2-(2'-hydroxyethyl)-1,4-diaminobenzene |
| 10.0000g | ammonia (25 percent aqueous solution) |
| 65.6444g | water |
| 100.0 | |

| Comparison Example IV | Hair Dye Solution |
|---|---|
| 10.0000g | of a mixture of the potassium salt of coconut oil fatty acid and oleic acid |
| 10.0000g | isopropanol |
| 2.5084g | 4-amino-2-(2'-hydroxyethyl)amino-5-chlorotoluene |
| 1.3518g | 1,4-diaminobenzene |
| 10.0000g | ammonia (25 percent aqueous solution) |
| 66.1398g | water |
| 100.0 | |

| Comparison Example V | Hair Dye Solution |
|---|---|
| 10.0000g | of a mixture of the potassium salt of coconut oil fatty acid and oleic acid |
| 10.0000g | isopropanol |
| 2.5084g | 4-amino-2-(2'-hydroxyethyl)amino-5-chlorotoluene |
| 1.5271g | 2,5-diaminotoluene |
| 10.0000g | ammonia (25 percent aqueous solution) |
| 65.9645g | water |
| 100.0 | |

| Comparison Example VI | Hair Dye Solution |
|---|---|
| 10.0000g | of a mixture of the potassium salt of coconut oil fatty acid and oleic acid |
| 10.0000g | isopropanol |
| 2.5084g | 4-amino-2-(2'-hydroxyethyl)amino-5-chlorotoluene |
| 1.9025g | 2-(2'-hydroxyethyl)-1,4-diaminobenzene |
| 10.0000g | ammonia (25 percent aqueous solution) |
| 65.5891g | water |
| 100.0 | |

| Comparison Example VII | Prior Art Hair Dye Solution |
|---|---|
| 10.0000g | of a mixture of the potassium salt of coconut oil fatty acid and oleic acid |
| 10.0000g | isopropanol |
| 2.0778g | 2,4-diamino-5-ethoxytoluene |

-continued

| | |
|---|---|
| 1.3518g | 1,4-diaminobenzene |
| 10.0000g | ammonia (25 percent aqueous solution) |
| 66.5704g | water |
| 100.0 | |
| Comparison Example VIII | Prior Art Hair Dye Solution |
| 10.0000g | of a mixture of the potassium salt of coconut oil fatty acid and oleic acid |
| 10.0000g | isopropanol |
| 2.0778g | 2,4-diamino-5-ethoxytoluene |
| 1.5271g | 2,5-diaminotoluene |
| 10.0000g | ammonia (25 percent aqueous solution) |
| 66.3951g | water |
| 100.0 | |
| Comparison Example IX | Prior Art Hair Dye Solution |
| 10.0000g | of a mixture of the potassium salt of coconut oil fatty acid and oleic acid |
| 10.0000g | isopropanol |
| 2.0778g | 2,4-diamino-5-ethoxytoluene |
| 1.9025g | 2-(2'-hydroxyethyl)-1,4-diaminobenzene |
| 10.0000g | ammonia (25 percent aqueous solution) |
| 66.0197g | water |
| 100.0 | |
| Comparison Example X | Prior Art Hair Dye Solution |
| 10.0000g | of a mixture of the potassium salt of coconut oil fatty acid and oleic acid |
| 10.0000g | isopropanol |
| 1.7520g | 2,4-diamino-5-fluorotoluene |
| 1.3518g | 1,4-diaminobenzene |
| 10.0000g | ammonia (25 percent aqueous solution) |
| 66.8962g | water |
| 100.0 | |
| Comparison Example XI | Prior Art Hair Dye Solution |
| 10.0000g | of a mixture of the potassium salt of coconut oil fatty acid and oleic acid |
| 10.0000g | oleic acid |
| 1.7520g | 2,4-diamino-5-fluorotoluene |
| 1.5271g | 2,5-diaminotoluene |
| 10.0000g | ammonia (25 percent aqueous solution) |
| 66.7209g | water |
| 100.0 | |
| Comparison Example XII | Prior Art Hair Dye Solution |
| 10.0000g | of a mixture of the potassium salt of coconut oil fatty acid and oleic acid |
| 10.0000g | isopropanol |
| 1.7520g | 2,4-diamino-5-fluorotoluene |
| 1.9025g | 2-(2'-hydroxyethyl)-1,4-diaminobenzene |
| 10.0000g | ammonia (25 percent aqueous solution) |
| 66.3455g | water |
| 100.0 | |

Each 5 g of the dye solution of Examples I to XII was mixed with 5 g of a 6-percent hydrogen peroxide solution shortly before use. The resulting mixture was then applied to white Buffalo hair strands. After acting for 30 minutes at 40° C. the Buffalo hair strands were rinsed with water and dried.

Subsequently the measured color values of the dyed Buffalo hair strands were obtained with a commercial colorimeter (Chromatometer CR 200 of the Minolta Firm). The brightness Y was measured relative to a pure white surface (Y=100%). The greater the Y-value, the brighter the color of the dyed Buffalo hair strands.

The parameters x, y and z indicate the proportion of red, green and blue shades in the color of the dyed hair strands.

The values of x and y were measured and the value of z was calculated from the formula $z=1-(x+y)$.

The measured color values of the dyed Buffalo hair strands are given in Table I hereinbelow (the color values measured after 3 weeks appear in parentheses).

TABLE I

| MEASURED COLOR VALUES FOR THE EXAMPLES | | | | |
|---|---|---|---|---|
| HAIR DYE SOLUTION | Y | x | y | z |
| Example I | 2.4 (2.6) | 0.239 (0.245) | 0.198 (0.210) | 0.563 (0.545) |
| Example II | 2.8 (2.8) | 0.227 (0.237) | 0.192 (0.208) | 0.581 (0.555) |
| Example III | 3.2 (3.2) | 0.223 (0.231) | 0.187 (0.200) | 0.584 (0.569) |
| Example IV | 2.3 (2.5) | 0.256 (0.266) | 0.226 (0.247) | 0.518 (0.487) |
| Example V | 2.9 (2.9) | 0.234 (0.254) | 0.201 (0.233) | 0.565 (0.513) |
| Example VI | 2.8 (2.8) | 0.228 (0.249) | 0.190 (0.224) | 0.582 (0.527) |
| Example VII | 2.5 (2.7) | 0.244 (0.261) | 0.209 (0.237) | 0.547 (0.502) |
| Example VIII | 3.2 (3.2) | 0.224 (0.247) | 0.191 (0.225) | 0.585 (0.528) |
| Example IX | 3.8 (3.8) | 0.223 (0.245) | 0.192 (0.221) | 0.595 (0.534) |
| Example X | 2.2 (2.4) | 0.240 (0.267) | 0.197 (0.244) | 0.563 (0.489) |
| Example XI | 2.5 (2.5) | 0.223 (0.266) | 0.181 (0.248) | 0.536 (0.486) |
| Example XII | 3.0 (3.0) | 0.219 (0.250) | 0.177 (0.227) | 0.604 (0.523) |

In the following it is proven that the 4-amino-2-(2'-hydroxyethyl)amino-4-chlorotoluene of the formula (A) has improved dye properties relative to its isomer 2-amino-4-(2'-hydroxyethyl)amino-5-chlorotoluene of the formula (B):

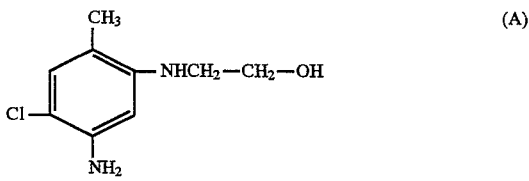

(A)

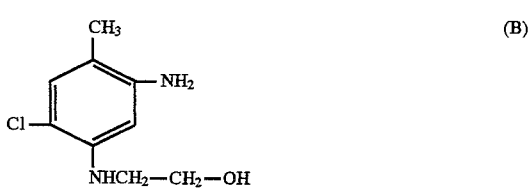

(B)

The dyed hair color obtained with the hair dye solution according to examples IV, V and VI was compared with the dyed hair color which was obtained with a hair dye solution in which the 4-amino-2-(2,-hydroxyethyl)amino-4-chlorotoluene according to the invention was replaced by an equivalent amount of its isomer, 2-amino-4-(2'-hydroxyethyl)amino-5-chlorotoluene (Examples IVa, Va and VIa). The measured color values which were obtained in the above-described manner are shown in the following Table II. The measurement value in parentheses was made 3 weeks after the hair dyeing process while the other value outside of the parentheses was obtained immediately after the hair dying process.

TABLE II

MEASURED COLOR VALUES FOR THE EXAMPLES

| HAIR DYE SOLUTION | Y | x | y | z |
|---|---|---|---|---|
| Example IV | 2.3 (2.5) | 0.256 (0.266) | 0.226 (0.247) | 0.518 (0.487) |
| Example V | 2.9 (2.9) | 0.234 (0.254) | 0.201 (0.233) | 0.565 (0.513) |
| Example VI | 2.8 (2.8) | 0.228 (0.249) | 0.190 (0.224) | 0.582 (0.527) |
| Example IVa | 2.7 (2.7) | 0.245 (0.288) | 0.208 (0.240) | 0.547 (0.472) |
| Example Va | 3.1 (3.4) | 0.231 (0.292) | 0.192 (0.235) | 0.577 (0.473) |
| Example VIa | 4.2 (4.2) | 0.227 (0.284) | 0.190 (0.225) | 0.583 (0.491) |

PRODUCTION EXAMPLES

Production Example A: Making of 4-amino-2-(2'-hydroxyethyl)amino-5-methoxytoluene Step 1: 2-amino-5-fluoro-4-nitrotoluene 1.3 g (10 mmol) of 4-fluoro-2-methylaniline were introduced into 10 ml of concentrated sulfuric acid and cooled to −10° C. A cold solution of 0.4 ml (10 mmol) of fuming nitric acid in 2 ml of concentrated sulfuric acid was added slowly dropwise. The resulting mixture was stirred for 3 hours at 0° C. and subsequently poured into ice. The precipitated product was filtered with suction and washed. 0.85 g (50% of the theoretical yield) of product was obtained. The yellow crystalline product had a melting point of 178° C.

$^1$H-NMR($D_6$-DMSO): δ=2.24 (s; 3H, —$CH_3$) 5.78 (br. s; 2H, —$NH_2$ exchange with $D_2O$) 7.28 (d, J=12 Hz; 1H, 6-H) 7.57 (d, J=6.8 Hz; 1H, 3-H)
MS (70ev): m/e=170($M^+$.)

Step 2: 2-chloroethyl-N-[(4-fluoro-2-methyl-5-nitro)phenyl]-carbamate 5 g (29 mmol) of 2-amino-5-fluoro-4-nitrotoluene was heated with 2.5 g calcium carbonate in 200 ml dioxan at 70° C., reacted with 3.1 ml of chloroformic acid chloroethyl ester and heated for 3 hours at 100° C. The resultant solution was filtered hot and the filtrate is introduced into 500 ml of ice water. The ocher colored precipitate was filtered with suction and recrystallized from an ethanol-water mixture. The resulting 6.6 g (81% of theoretical) of 2-chloroethyl-N-[(4-fluoro-2-methyl-5-nitro)phenyl]-carbamate had a melting point of 113° C.

$^1$H-NMR($D_6$-DMSO): δ=2.33 (s; 3H, —$CH_3$) 3.88 (t; 2H, —$CH_2Cl$) 4.38 (t; 2H, —$CH_2CH_2Cl$) 7.49 (d, J=12.3 Hz; 1H, 6-H) 8.22 (d, J=7.3 Hz; 1H, 3-H) 9.44 (br.s; 2H, —NH, exchange with $D_2O$)
MS(70ev): m/e=276($M^+$.)

Step 3: 2-(2'-hydroxyethyl)amino-4-nitro-5-methoxytoluene 10 g of (36 mmol) of 2-chloroethyl-N-[4-fluoro-2-methyl-5-nitro)phenyl]-carbamate were reacted with 120 ml of a mixture of 10 percent NaOH and methanol in a ratio of 2:1 and heated for one hour under reflux. After cooling the solution was diluted with water and neutralized with acetic acid. The fine red product crystals were filtered off from the solution and recrystallized from an ethanol-water mixture. The product yield (5.1 g) was 63% of the theoretical yield and the melting point was 94° C.

$^1$H-NMR($D_6$-DMSO): δ=2.24 (s; 3H, —$CH_3$) 3.16–3.22 (m; 2H, —$CH_2OH$) 3.64–3.66 (m; 2H, —$NHCH_2$) 3.86 (s; 3H, —$OCH_3$) 4.82 (br.s; 1H, —OH, exchange with $D_2O$) 4.93 ( br.; 1H, —NH, exchange with $D_2O$) 7.04 (s; 1H, 6-H)
7.15 (s; 1H, 3-H)
MS(70ev): m/e=226($M^+$.)

Step 4: 4-amino-2-(2'-hydroxyethyl)amino-5-methoxytoluene 3 g ( 15 mmol) of 2-(2'-hydroxyethyl)amino-4-nitro-5-methoxytoluene were hydrogenated using a catalytic amount of Palladium/Carbon (5% Pd) in 100 ml absolute ethanol. After filtration of the catalyst the solvent was completely distilled away and the green crystals were recrystallized from methanol. 2.2 g (83% of the theoretical yield) of the 4-amino-2-(2'-hydroxyethyl)amino-5-methoxytoluene were obtained and melted at 148° C.

$^1$H-NMR($D_6$-DMSO): δ=2.01 (s; 3H, —$CH_3$) 3.06 (m; 2H, —$CH_2OH$) 3.61–3.66 (m; 2H, —$NHCH_2$) 3.68 (s; 3H, —$OCH_3$) 4.08 (br.s; 1H, —OH, exchange with $D_2O$) 4.37 (br.s; 2H, —$NH_2$, exchange with $D_2O$) 4.76 (br.s; 1H, —NH, exchange with $D_2O$) 6.05 (s; 1H, 3-H) 6.55 (s; 1H, 6-H)
MS(70ev): m/e=196($M^+$.)

Production Example B: Making of 4-amino-2-(2'-hydroxyethyl)amino-5-ethoxytoluene Steps 1 and 2: 2-chloroethyl-N-[(4-fluoro-2-methyl-5-nitro)phenyl]-carbamate 2-chloroethyl-N-[4-fluoro-2-methyl-5-nitro)phenyl]-carbamate was made in the same way as in steps 1 and 2 of Production Example A from 4-fluoro-2-methyl aniline.

Step 3: 2-(2'-hydroxyethyl)amino-5-ethoxy-4-nitrotoluene 11 g (3.6 mmol) of 2-chloroethyl-N-[(4-fluoro-2-methyl-5-nitro)phenol]-carbamate in 10 ml of ethanol and 10 ml of 10 percent aqueous sodium hydroxide solution were heated for one hour under reflux. The resulting solution was introduced to ice and was neutralized with acetic acid. The red precipitate was filtered off from the solution. The yield of product amounted to 0.7 g (80% theoretical yield) and the melting point was 119° C.

$^1$H-NMR($D_6$-DMSO): δ=1.31 (t, J=7.0 Hz; 3H, —$OCH_2CH_3$) 2.17 (s; 3H, —$CH_3$) 3.10–3.16 (m; 2H, —$CH_2OH$) 3.58 (m; 2H, —$NHCH_2$) 4.04–4.08 (q, J=6.9 Hz; 2H, —$OCH_2CH_3$) 4.78 (br.s; 1H, —NH) 4.90 (t, J=5.6 Hz; 1H, —OH) 6.96 (s; 1H, 6-H) 7.08 (s; 2H, 3-H)
MS(70ev): m/e=240($M^+$.)

Step 4: 4-amino-2-(2'-hydroxyethyl)amino-5-ethoxytoluene 644 mg (2.7 mmol) of 2-(2'-hydroxyethyl)amino-5-ethoxy-4-nitrotoluene were hydrogenated with a catalytic amount of palladium/active carbon (5% Pd) in 50 ml methanol. After filtering off the catalyst, the solvent was completely distilled away. 428 mg (76% of theoretical yield) of 4-amino-2-(2'-hydroxyethyl)amino-5-ethoxytoluene were obtained in pure form by thin layer chromatography. The obtained product crystals melted at 128° C.

$^1$H-NMR ($D_6$-DMSO): δ=1.26 (t, 3H, —$OCH_2CH_3$) 1.94 (s; 3H, —$CH_3$) 2.98 (m; 2H, —$CH_2OH$) 3.57 (m; 2H, —$NHCH_2$) 3.79–3.86 (q; 2H, $OCH_2CH_3$) 4.12 (br.s; 1H, —OH, exchange with $D_2O$) 4.69 (br.s; 1H, —NH, exchange with $D_2O$) 5.98 (S; 1H, 3-H) 6.48 (s; 1H, 6-H)
MS(70ev): m/e=210($M^+$.)

Production Example C: Making of 4-amino-2-(2'-hydroxyethyl)amino-5-chlorotoluene hydrochloride Step 1: 2-amino-5-chloro-4-nitrotoluene 7 g (20 mmol) of 2-amino-5-chlorotoluene were dissolved in 10 ml of sulfuric acid at 10° C. to form a reactant solution. 2.05 ml fuming nitric acid were dissolved in 10 ml concentrated sulfuric acid and the resultant acidic solution was added slowly dropwise to the reactant solution. The reactant solution was then stirred for 3 to 4 hours at room temperature and subsequently added to ice. The yellow product crystals were filtered with suction and recrystallized from methanol. 6.4 g (70% of the theoretical yield) of 2-amino-5-chloro-4-nitrotoluene, which melted at 115° C., were obtained.

$^1$H-NMR($D_6$-DMSO): δ=2.13 (s; 3H, —$CH_3$) 4.24 (br.s; 2H, —$NH_2$) 7.26 (s, 2H, 3-H, 6-H)
MS(70ev): m/e=141($M^+$.)

Step 2: 2-chloroethyl-N-[(4-chloro-2-methyl-5-nitro)phenyl]-carbamate 3 g (16 mmol) of 4-amino-5-chlorotoluene were heated in 150 ml dioxan with 1.5 g of calcium carbonate at 70° C. 3.6 ml (35 mmol) of chloroformic acid chloroethylester were added dropwise and the resulting solution was stirred for 3.5 hours at 100° C. This solution was filtered, introduced to ice and the resultant bright crystals were obtained by filtration with suction. 4.5 g (94% of the theoretical yield) of 2-chloroethyl-N-[(4-chloro-2-methyl-5 -nitro)phenyl]-carbamate were obtained. These product crystals melted at 93° C.

$^1$H-NMR ($D_6$-DMSO): δ=2.33 (s; 3H, —$CH_3$) 3.87 (t; J=5.2 Hz; 2H, —$CH_2$Cl) 4.39 (t; J=5.2 Hz; 3H, —$CH_2CH_2$Cl) 7.59 (s; 1H, 6-H) 8.23 (s; 1H, 3-H) 9.51 (br.s; 1H, —NH)
MS(70ev): m/e=293 ($M^+$.)

Step 3: 2-(2'-hydroxyethyl)amino-4-nitro-5-chlorotoluene 2 g (6.8 mmol) of 2-chloroethyl-N-[(4-chloro-2-methyl-5-nitro)phenyl]-carbamate were heated in 10 ml of methanol at 70° C. 8.2 ml (21 mmol) of 10 percent sodium hydroxide was added dropwise and the resultant mixture was heated under reflux for 1.5 hours. The solution was introduced into ice and neutralized with acetic acid. The precipitate arising was filtered and recrystallized from ethanol/water. 816 mg (52% of the theoretical yield) of orange crystals were obtained and melted at 110° C. $^1$H-NMR ($D_6$-DMSO): δ=2.15 (s; 3H, —$CH_3$) 3.22 (q, J=5.7 Hz; 2H, —$CH_2$OH) 3.58 (q, J=5.8 Hz; 2H, —$NHCH_2$) 4.78 (t, J=5.6 Hz; 1H, —OH, exchange with $D_2$O) 5.53 (t, J=5.3 Hz; 1H, —NH, exchange with $D_2$O) 7.11 (s; 1H, 6-H) 7.29 (s; 1H, 3-H)
MS(70ev): m/e=230($M^+$.)

Step 4: 4-amino-2-(2'-hydroxyethyl) amino-5-chlorotoluene hydrochloride 670 mg (2.9 mmol) of 2-(2'-hydroxyethyl)amino-5-chloro-4-nitrotoluene and 625 g of tin in 10 ml semiconcentrated hydrochloric acid were heated under reflux for one hour. After cooling, this mixture was diluted with 10 ml of water and 40 ml of 10 percent aqueous sodium hydroxide solution were added. The tin salt precipitate was filtered off and the filtrate was extracted 3 times with 30 ml of methylene chloride each time. After washing with water the filtrate was dried over sodium sulfate and the solvent was completely distilled away. The oily residue was received in 20 ml of methanol and reacted with an equimolar amount of hydrochloric acid.

$^1$H-NMR ($D_6$-DMSO): δ=1.93 (s; 3H, —$CH_3$) 3.05 (t, J=6.0 Hz; 2H, —$CH_2$OH) 3.33 (br.s; 1H, —OH, exchange with $D_2$O) 3.59 (t, J=5.9 Hz; 2H, —$NHCH_2$) 4.72 (br.s; 2H, —$NH_2$, exchange with $D_2$O) 5.1 (br.s; 1H, —NH, exchange with $D_2$O) 6.75 (S; 1H, 3-H) 6.95 (S; 1H, 6-H)
MS(70ev): m/e=200($M^+$.)

All values in percent are percent by weight unless indicated otherwise.

While the invention has been illustrated and described as embodied in substituted 2-alkylamino-4-amino-1-alkylbenzene compounds and oxidation hair dye compositions based on these compounds, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. An oxidation hair dye composition containing an effective amount of at least one developer substance and an effective amount of at least one coupler substance selected from the group consisting of 4-amino-2-(2'-hydroxyethyl)amino-5-methoxytoluene and 4-amino-2-(2'-hydroxyethyl)amino-5-chlorotoluene.

2. An oxidation hair dye composition as defined in claim 1, containing from 0.01 to 5 percent by weight of said at least one coupler substance.

3. An oxidation hair dye composition as defined in claim 1, wherein said at least one developer substance is selected from the group consisting of 1,4-diaminobenzene, 2,5-diaminotoluene, 2-(2'-hydroxyethyl)-1,4-diaminobenzene, 4-aminophenol, 4-amino-2-aminomethylphenol, 4-amino-3-methylphenol, 4-amino- 2-methoxymethylphenol, 4-amino-2-ethoxymethylphenol, 4,5-diamino-1-methylpyrazole, 4,5-diamino-1-isopropyl pyrazole, 1-benzyl-4,5-diamino pyrazole, 4,5-diamino-1-methylbenzyl pyrazole and tetraaminopyrimidine and physiologically compatible salts thereof.

4. An oxidation hair dye composition as defined in claim 1, having a total content of said at least one developer substance and said at least one coupler substance of from 0.1 to 5.0 percent by weight.

5. An oxidation hair dye composition as defined in claim 1, containing at least one dye component selected from the group consisting of 6-amino-2-methylphenol, 2-amino-5-methylphenol, 4-[(4'-aminophenyl)-(4"-imino-2",5"-cyclohexadien-1"-yliden)-methyl]-2-methylaminobenzene monohydrochloride, 4-[(4'-amino-3'-methylphenyl)-(4"-imino-3"-methyl-2",5"-cyclohexadien-1"-yliden)methyl]-2-methylaminobenzene monohydrochloride, 2-amino-4,6-dinitrophenol, 2-amino-5-(2'-hydroxy-ethylamino)-nitrobenzene, 4-(2'-hydroxyethylamino)-3-nitrotoluene, 1-(2'-ureidoethyl)amino-4-nitrobenzene, 7-[(4'-aminophenyl)azo]-8-hydroxynaphthalen-4-sulfonic acid sodium salt, 1,4-diaminoanthraquinone and 1,4,5,8-tetraaminoanthraquinone.

6. 4-amino-2-(2'-hydroxyethyl)amino-5-methoxytoluene.

7. 4-amino-2-(2'-hydroxyethyl)amino-5-chlorotoluene.

* * * * *